United States Patent
Singh

(10) Patent No.: US 10,391,206 B2
(45) Date of Patent: Aug. 27, 2019

(54) CANNULA FOR EXTERNAL DRAINAGE OF SUBRETINAL FLUID

(71) Applicant: University of Kansas, Lawrence, KS (US)

(72) Inventor: Ajay Singh, Mission Hills, KS (US)

(73) Assignee: University of Kansas, Lawrence, KS (US)

( * ) Notice: Subject to any disclaimer, the term of this patent is extended or adjusted under 35 U.S.C. 154(b) by 0 days.

(21) Appl. No.: 15/328,385

(22) PCT Filed: Jul. 30, 2015

(86) PCT No.: PCT/US2015/042942
§ 371 (c)(1),
(2) Date: Jan. 23, 2017

(87) PCT Pub. No.: WO2016/019160
PCT Pub. Date: Feb. 4, 2016

(65) Prior Publication Data
US 2017/0216092 A1 Aug. 3, 2017

Related U.S. Application Data

(60) Provisional application No. 62/031,065, filed on Jul. 30, 2014.

(51) Int. Cl.
*A61M 1/00* (2006.01)
*A61B 17/34* (2006.01)
(Continued)

(52) U.S. Cl.
CPC ....... *A61M 1/0003* (2013.01); *A61B 17/3478* (2013.01); *A61F 9/00727* (2013.01);
(Continued)

(58) Field of Classification Search
CPC ............ A61M 1/0003; A61M 25/0068; A61M 25/007; A61M 25/01; A61M 25/0113; A61M 25/0693; A61M 2025/0175; A61M 2025/018; A61M 2025/0183; A61M 2025/0681; A61M 2025/0687;
(Continued)

(56) References Cited

U.S. PATENT DOCUMENTS 1,453,309 A * 5/1923 Eberly, Jr. ............... A61M 5/46
604/117
2,187,259 A * 1/1940 Barnhart ................. A61M 5/32
604/117

(Continued)

OTHER PUBLICATIONS

International Search Report and Written Opinion of PCT/US2015/042942, dated Nov. 2, 2015.

*Primary Examiner* — Kami A Bosworth
(74) *Attorney, Agent, or Firm* — Ray Quinney & Nebeker P.C.; Paul N. Taylor

(57) ABSTRACT

A cannula device for draining sub-retinal fluid externally to the eye includes a shaft, an outer sleeve, and an inner sleeve. The outer sleeve and the inner sleeve have a curve therein to access the back of the eye externally. The outer sleeve is extendable relative to the inner sleeve and the shaft, and the outer sleeve includes a penetrative tip to penetrate the sclera and provide access to the sub-retinal fluid to the inner sleeve.

20 Claims, 8 Drawing Sheets

(51) Int. Cl.
*A61F 9/007* (2006.01)
*A61M 25/01* (2006.01)

(52) U.S. Cl.
CPC ......... *A61F 9/00736* (2013.01); *A61M 25/01* (2013.01); *A61M 25/0113* (2013.01); *A61M 2025/0175* (2013.01)

(58) Field of Classification Search
CPC ...... A61M 2210/0612; A61M 25/0612; A61M 25/0643; A61M 2025/009; A61M 5/46; A61F 9/007; A61F 9/00709; A61F 9/00727; A61F 9/00736; A61B 17/3478; A61B 17/3494; A61B 17/3496; A61B 5/150534
See application file for complete search history.

(56) References Cited

U.S. PATENT DOCUMENTS

| | | | | |
|---|---|---|---|---|
| 2,409,979 | A * | 10/1946 | Huber | A61M 5/3286 |
| | | | | 604/274 |
| 2,737,948 | A * | 3/1956 | Brown | A61M 5/288 |
| | | | | 604/192 |
| 3,605,744 | A * | 9/1971 | Dwyer | A61M 5/2033 |
| | | | | 604/139 |
| 4,099,528 | A | 7/1978 | Sorenson et al. | |
| 4,518,383 | A * | 5/1985 | Evans | A61B 17/3401 |
| | | | | 604/170.03 |
| 4,717,383 | A * | 1/1988 | Phillips | A61M 5/204 |
| | | | | 604/135 |
| 5,100,390 | A * | 3/1992 | Lubeck | A61B 17/3401 |
| | | | | 604/158 |
| 5,195,964 | A | 3/1993 | Kletzky et al. | |
| 5,665,072 | A * | 9/1997 | Yoon | A61B 17/3417 |
| | | | | 604/164.12 |
| 5,817,075 | A | 10/1998 | Giungo | |
| 6,200,291 | B1 * | 3/2001 | Di Pietro | A61M 5/46 |
| | | | | 604/117 |
| 6,425,887 | B1 * | 7/2002 | McGuckin | A61B 17/3417 |
| | | | | 604/272 |
| 6,485,475 | B1 * | 11/2002 | Chelly | A61M 25/065 |
| | | | | 604/164.01 |
| 6,802,829 | B2 * | 10/2004 | Buono | A61F 9/0017 |
| | | | | 604/187 |
| 7,122,042 | B2 | 10/2006 | LoRusso | |
| 7,316,676 | B2 | 1/2008 | Peyman et al. | |
| 7,485,113 | B2 | 2/2009 | Varner et al. | |
| 8,267,890 | B2 * | 9/2012 | Alchas | A61M 5/3129 |
| | | | | 604/115 |
| 8,425,473 | B2 | 4/2013 | Ho et al. | |
| 2001/0044606 | A1 * | 11/2001 | Inkpen | A61M 5/3287 |
| | | | | 604/181 |
| 2002/0173816 | A1 * | 11/2002 | Hung | A61B 10/0045 |
| | | | | 606/194 |
| 2003/0120222 | A1 * | 6/2003 | Vaillancourt | A61M 5/321 |
| | | | | 604/263 |
| 2003/0158519 | A1 * | 8/2003 | Epstein | A61B 17/3478 |
| | | | | 604/116 |
| 2004/0116892 | A1 | 6/2004 | Burroughs et al. | |
| 2004/0267211 | A1 * | 12/2004 | Akahoshi | A61F 9/00745 |
| | | | | 604/264 |
| 2005/0261693 | A1 * | 11/2005 | Miller | A61B 17/32002 |
| | | | | 606/80 |
| 2007/0106300 | A1 | 5/2007 | Auld et al. | |
| 2008/0195135 | A1 | 8/2008 | Attinger | |
| 2008/0215078 | A1 * | 9/2008 | Bennett | A61B 17/3417 |
| | | | | 606/166 |
| 2009/0259179 | A1 * | 10/2009 | Hillios | A61M 5/46 |
| | | | | 604/110 |
| 2010/0010468 | A1 * | 1/2010 | Becker | A61M 5/329 |
| | | | | 604/506 |
| 2010/0185161 | A1 * | 7/2010 | Pellegrino | A61B 17/3472 |
| | | | | 604/272 |
| 2012/0046664 | A1 | 2/2012 | McGuckin, Jr. et al. | |
| 2012/0191064 | A1 * | 7/2012 | Conston | A61F 9/00727 |
| | | | | 604/506 |
| 2015/0112278 | A1 * | 4/2015 | Ray | A61M 25/065 |
| | | | | 604/240 |

* cited by examiner

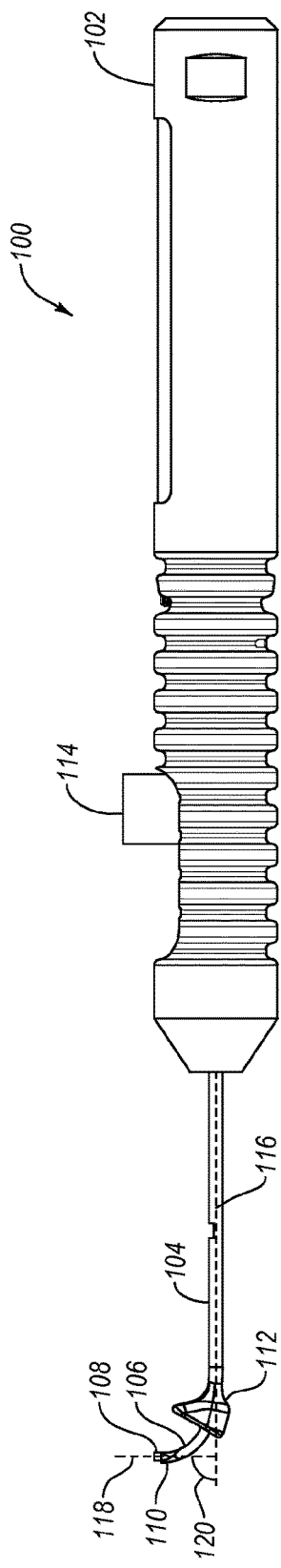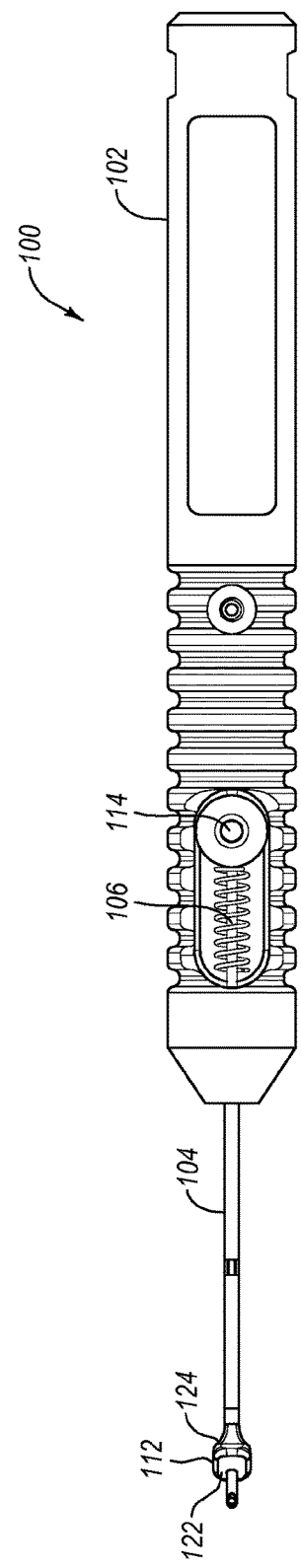

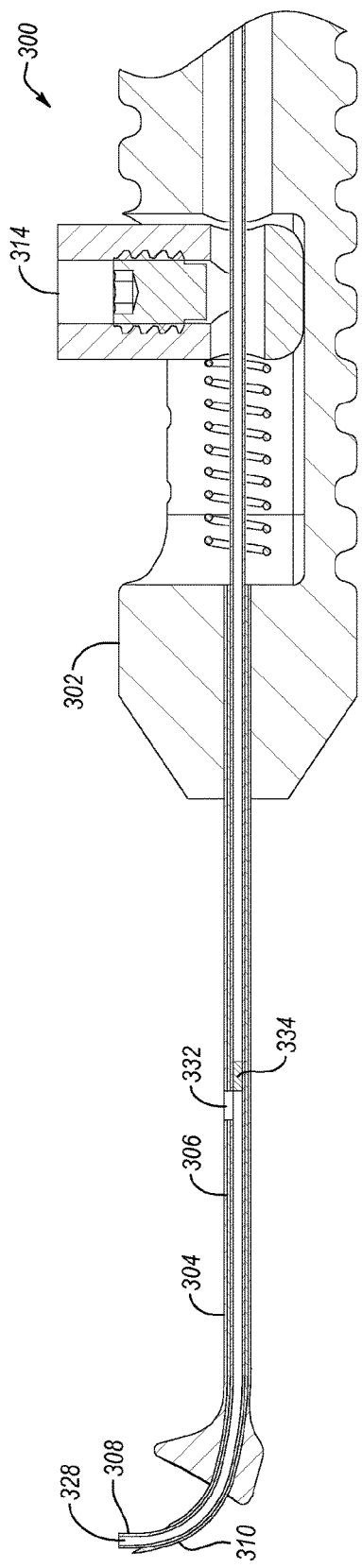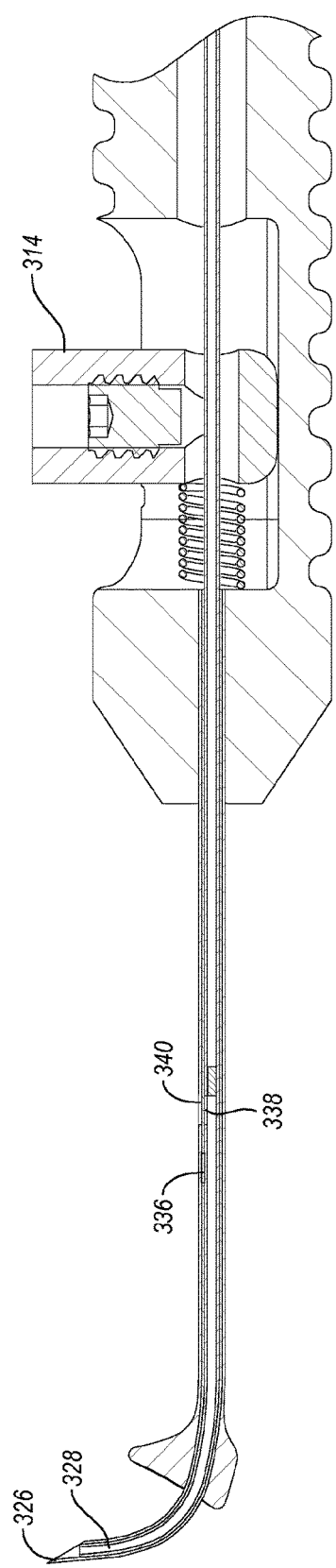
FIG. 5
FIG. 6

CANNULA FOR EXTERNAL DRAINAGE OF SUBRETINAL FLUID

CROSS-REFERENCE TO RELATED APPLICATIONS

This application is a U.S. Nationalization of PCT Application Number PCT/US2015/042942, filed on Jul. 30, 2015, which claims priority to and the benefit of U.S. Provisional Patent Application 62/031,065 filed Jul. 30, 2014, entitled "SUBRETINAL CANNULA FOR OPHTHALMIC USE," the disclosures of which are incorporated herein by reference in their entireties.

BACKGROUND OF THE DISCLOSURE

A variety of ocular surgery requires the drainage or removal of retinal fluid. In particular, subretinal fluid ("SRF") is drained during surgical repair of retinal detachment ("RD") in scleral buckling surgery, pars plana vitrectomy, or pneumatic retinopexy. More recently, surgical procedures have been developed to inject fluids and stem cells under the retina to treat certain degenerative retinal conditions.

RD is a condition where intraocular fluid passes under the retina from a hole within the retina. The intraocular fluid enters a space between the retina and the choroid. Once between the retina and the choroid, the SRF lifts up the retina, causing the retina to come away from its normal attachment to the choroid at the back of the eye. RD can lead to irreversible blindness in the patient if the retina is not fixed in a timely manner. In certain other conditions when there is inflammation in the eye, the retina may have SRF develop under the retina without a hole. The end result is the same where it results in irreversible blindness.

RD may be conventionally addressed using scleral buckling, pars plana ("PP") vitrectomy, or pneumatic retinopexy. Scleral buckling includes the application of a silicone sponge, rubber, or semi-hard plastic to the exterior of the sclera by the operating professional. Conventionally, the buckling element is left in place permanently. The buckling element compresses the sclera toward the center of the eye, relieving traction on the retina, allowing the RD to settle against the wall of the eye.

Pars plana vitrectomy includes the removal of vitreous fluid from the vitreous chamber of the eye behind the lens. The vitreous fluid is conventionally removed through the pars plana adjacent the iris and ciliary body. To fix a RD via the pars plana vitrectomy route disadvantageously involves the penetration of the retina to provide a drainage path of the SRF.

Pneumatic retinopexy includes the introduction of a gas bubble having a different density than the vitreous fluid in the eye. The buoyancy of the gas bubble in the vitreous fluid enables the gas bubble to apply a force to the detached portion of the retina and urge the retina back into the proper position. More importantly, the gas bubble closes the retinal hole thereby preventing further entry of vitreous fluid under the retina. The retina is then secured via cryopexy, photocoagulation, or other fixation method.

In each procedure, the removal of the SRF allows the proper placement of the retina apposed against the inside of the back of the eye and allows the retina to be more reliably secured in place. Incomplete removal of the SRF results in the inability of the retina to function leading to blindness. Additionally, any further damage to the retina can introduce additional holes or tears through which intraocular fluid may reenter the space behind the retina, resulting in an increased risk of RD. Therefore, a device and method for the reliable and complete removal of SRF from behind the retina is desirable.

BRIEF SUMMARY OF THE DISCLOSURE

This summary is provided to introduce a selection of concepts that are further described below in the detailed description. This summary is not intended to identify specific features of the claimed subject matter, nor is it intended to be used as an aid in limiting the scope of the claimed subject matter.

In an embodiment, a cannula device includes a shaft, an outer sleeve within the shaft, and an inner sleeve within the outer sleeve. The shaft has a longitudinal axis. The outer sleeve is longitudinally slidable relative to the inner sleeve. The outer sleeve has a penetrative tip that protrudes distally from the shaft. The penetrative tip defines a distal axis at angle to the longitudinal axis in a range of 30° to 90°. A guard connected to the shaft extends transversely to the shaft.

In another embodiment, a cannula device includes a handle, a shaft extending from the handle, an outer sleeve partially within the shaft, and an inner sleeve at least partially in the outer sleeve. The outer sleeve is longitudinally slidable relative to the shaft and having a penetrative tip at a distal end. The position of the outer sleeve relative to the shaft is at least partially determined by the control member. The shaft has a deflection portion that defines a distal axis at an angle to the longitudinal axis in a range of 30° to 90°. The inner sleeve is longitudinally stationary relative to the shaft. A guard is connected to the shaft and extends radially away from the shaft. The guard has a curved distal surface and a proximal surface.

In yet another embodiment, a cannula device includes a shaft, a flexible outer sleeve partially within the shaft, and an inner sleeve at least partially in the outer sleeve. The outer sleeve is longitudinally slidable relative to the shaft and having a penetrative tip at a distal end. The position of the outer sleeve relative to the shaft is at least partially determined by the control member. The shaft has a deflection portion that defines a distal axis at an angle to the longitudinal axis in a range of 30° to 90°. The inner sleeve is longitudinally stationary relative to the shaft. A guard is connected to the shaft and extends radially away from the shaft. The guard has a curved distal surface and a proximal surface. The outer sleeve is slidably movable between a retracted position and an inserted position. The inner sleeve protrudes distally from the penetrative tip when the outer sleeve is in the retracted position.

Additional features of embodiments of the disclosure will be set forth in the description which follows. The features of such embodiments may be realized by means of the instruments and combinations particularly pointed out in the appended claims. These and other features will become more fully apparent from the following description and appended claims, or may be learned by the practice of such exemplary embodiments as set forth hereinafter.

BRIEF DESCRIPTION OF THE DRAWINGS

In order to describe the manner in which the above-recited and other features of the disclosure can be obtained, a more particular description will be rendered by reference to specific embodiments thereof which are illustrated in the appended drawings. For better understanding, the like elements have been designated by like reference numbers throughout the various accompanying figures. While some of the drawings may be schematic or exaggerated representations of concepts, at least some of the drawings may be drawn to scale. Understanding that the drawings depict some example embodiments, the embodiments will be described and explained with additional specificity and detail through the use of the accompanying drawings in which:

FIG. 1 is a side view of an embodiment of a cannula device, according to the present disclosure;

FIG. 2 is a top view of the cannula device of FIG. 1, according to the present disclosure;

FIG. 5 is a side cross-sectional view of an embodiment of a cannula device having a lateral fluid port therein, according to the present disclosure;

FIG. 6 is a side cross-sectional view of the cannula device of FIG. 5 having the outer sleeve moved distally beyond the inner sleeve, according to the present disclosure;

DETAILED DESCRIPTION

Figure 3:
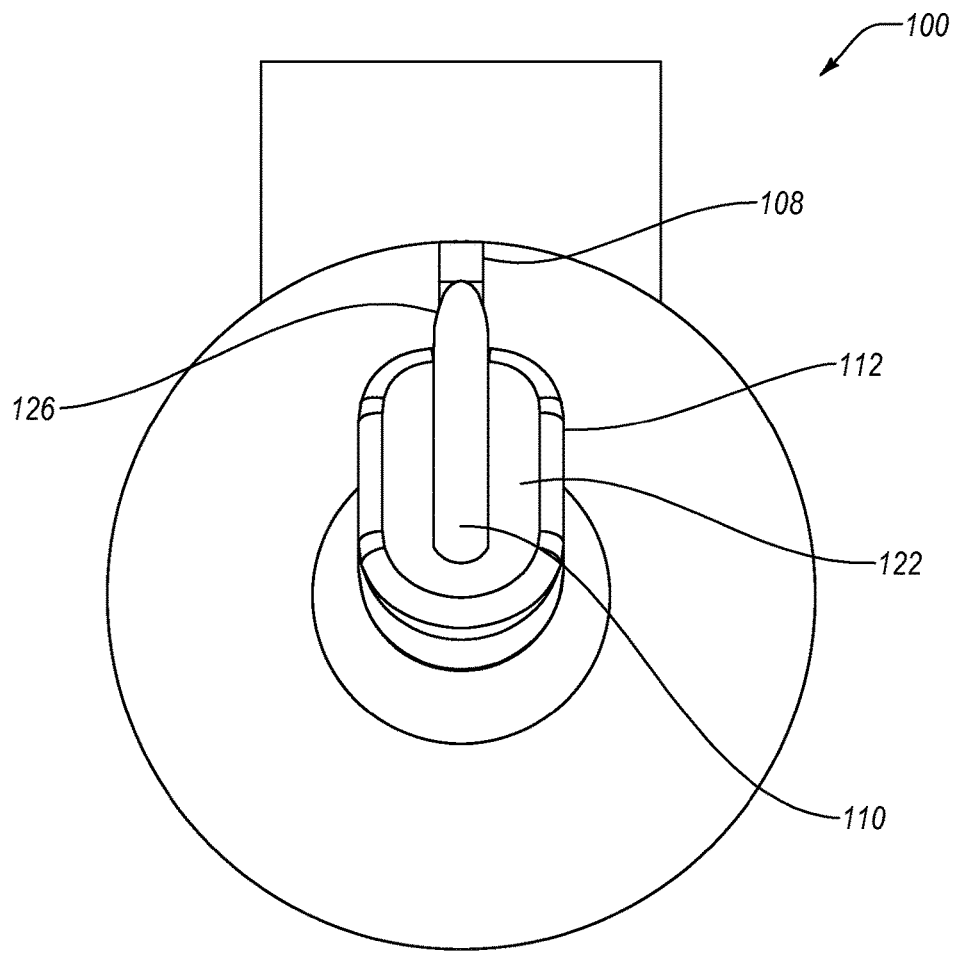
FIG. 3 is a front view of the cannula device of FIG. 1, according to the present disclosure.

One or more specific embodiments of the present disclosure will be described below. In an effort to provide a concise description of these embodiments, some features of an actual embodiment may be described in the specification. It should be appreciated that in the development of any such actual embodiment, as in any engineering or design project, numerous embodiment-specific decisions will be made to achieve the developers' specific goals, such as compliance with system-related and business-related constraints, which may vary from one embodiment to another. It should further be appreciated that such a development effort might be complex and time consuming, but would nevertheless be a routine undertaking of design, fabrication, and manufacture for those of ordinary skill having the benefit of this disclosure.

One or more embodiments of the present disclosure may generally relate to constructing and using a cannula device for use in medical procedures. More specifically, the present disclosure may relate to constructing and using a cannula device for the draining of sub-retinal fluid ("SRF") from the eye. SRF is located behind the retina of a patient's eye and in the region of the eye where the retina has detached. The SRF may accumulate between the retina and the sclera, the fibrous outer layer of the eye. A cannula device may provide a fluid conduit through the sclera in the back of the eye to allow drainage of the SRF without penetrating the retina. Penetration of the retina may delay and/or complicate recovery from the drainage of the SRF and reattachment of the detached retina. Penetration of the retina requires entry into the eye from the pars plana route using a vitrectomy technique.

A cannula device may include a handle with a shaft extending therefrom in a distal direction. The shaft may house an inner sleeve and an outer sleeve. The inner sleeve may provide a fluid conduit to drain the SRF from the eye. The outer sleeve may have a penetrative distal end that may penetrate the sclera and provide an opening therethrough. The inner sleeve may be introduced to the eye through the opening, and SRF may be drained therethrough. The outer sleeve may be retracted proximally after penetrating the sclera and prior to and/or while introducing the inner sleeve such that the fluid conduit may be provided to drain the SRF while reducing the risk that the penetrative distal end of the outer sleeve may damage the retina. The SRF may be drained into a fluid compartment in the handle, or through a lateral port in the shaft.

FIG. 1 depicts a side view of an embodiment of a cannula device 100, according to the present disclosure. The cannula device 100 may include a handle 102 having a shaft 104 extending longitudinally therefrom in a distal direction. In some embodiments, the shaft 104 may be substantially tubular, having an open space in the center thereof, allowing other components to be positioned and/or moved within the shaft 104. In other embodiments, the shaft 104 may have non-circular transverse cross-sections, such as rectangular, square, octagonal, elliptical, other regular shapes, irregular shapes, or combinations thereof.

The shaft 104 may house an outer sleeve 106 therein. The outer sleeve 106 may be longitudinally slidable relative to the shaft 104. In some embodiments, the outer sleeve 106 may be made of or include a flexible and/or resilient material such that the outer sleeve 106 may have a curved and/or angled portion. The outer sleeve 106 may bend and/or flex upon longitudinal movement of the outer sleeve 106 relative to the shaft 104 and may recover an original shape thereafter. In other embodiments, the outer sleeve 106 may include a shape memory material. For example, the outer sleeve 106 may be made of or include a nickel titanium alloy. In another example, the outer sleeve 106 may include a shape memory polymer.

The outer sleeve 106 may house an inner sleeve 108 therein. The inner sleeve 108 may be longitudinally fixed relative to the shaft 104. The inner sleeve 108 may protrude distally from the outer sleeve 106 when the outer sleeve 106 is moved proximally and may be covered by the outer sleeve 106 when the outer sleeve 106 is moved distally. The inner sleeve 108 may provide a fluid conduit through which a fluid may be drained during a medical procedure, such as ocular surgery. While the cannula device 100 may be described in relation to ocular surgery and, in particular, retinal detachment ("RD"), the cannula device 100 may be used in other procedures to remove fluids. The cannula device 100 also may be used to inject fluid under the retina from the exterior of the eye such as in delivering medication into the sub retinal space.

To provide fluid communication between an eye cavity and the fluid conduit of the inner sleeve 108, the outer sleeve 106 may include a penetrative tip 110 at the distal end of the outer sleeve 106. The outer sleeve 106 may be moved distally to extend beyond the inner sleeve 108 and penetrate the sclera of the eye and allow the inner sleeve 108 to enter the eye cavity. The penetrative tip 110 may include a beveled edge, a tapered edge, a serrated edge, or combinations thereof to facilitate penetration of bodily materials.

To position the inner sleeve 108 and the penetrative tip 110 of the outer sleeve 106 relative to the eye cavity, the cannula device 100 may include a guard 112 extending transversely from the shaft 104. In some embodiments, the guard 112 may be positioned to allow a chord length (i.e., length of the inner sleeve 108 extending distally of the guard 112) in a range having upper and lower values including any of 2.0 millimeters (mm), 2.25 mm, 2.5 mm, 2.75 mm, 3.0 mm, 3.25 mm, 3.5 mm, 3.75 mm, 4.0 mm, 4.25 mm, 4.5 mm, or any value therebetween. For example, the chord length may be in a range of 2.0 mm to 4.5 mm. In another example, the chord length may be in a range of 2.5 mm to 4.25 mm. In yet another example, the chord length may be in a range of 3.0 mm to 4.0 mm.

The position of the outer sleeve 106 relative to the shaft 104 and, hence, the position of the penetrative tip 110 relative to the inner sleeve 108 may be controlled by a control member 114 protruding from and/or positioned in the handle 102. The control member 114 may allow for the direct or indirect longitudinal positioning of the outer sleeve 106. In some embodiments, the control member 114 may be operably connected to the outer sleeve 106 by an adhesive, a mechanical connection (e.g., bolt, clamp, screw), a mechanical linkage, an integral connection (e.g., brazing, welding), or combinations thereof. In other embodiments, the control member 114 may be integrally formed with the outer sleeve 106. In some embodiments, moving the control member 114 distally may move the outer sleeve 106 distally and moving the control member 114 proximally may move the outer sleeve 106 proximally. In other embodiments, the movement and/or position of the outer sleeve 106 may be biased by a biasing member. For example, the movement and/or position of the outer sleeve 106 may be biased by a spring, a magnet, a compressible gas, a roller mechanism, or other biasing member that applies a proximal force to the outer sleeve 106 to urge the outer sleeve 106 in the proximal direction. In such an example, a user may apply a distal force to the control member 114 to overcome the proximal force of the biasing member and move the outer sleeve 106 distally. For example, the penetrative tip 110 may extend beyond the inner sleeve 108 while the user applies a distal force to the control member 114 and, upon releasing the distal force on the control member 114, the outer sleeve 106 may move proximally at least partially due to the biasing member.

In some embodiments, the shaft 104 may have a length in a range having upper and lower values including any of 2.0 centimeters (cm), 2.1 cm, 2.2 cm, 2.3 cm, 2.4 cm, 2.5 cm, 2.6 cm, 2.7 cm, 2.8 cm, 2.9 cm, 3.0 cm, or any value therebetween. For example, the shaft 104 may have a length in a range of 2.0 cm to 3.0 cm. In another example, the shaft 104 may have a length in a range of 2.4 cm to 2.8 cm. In yet another example, the shaft 104 may have a length of about 2.6 cm. In some embodiments, the shaft 104 may include a longitudinal axis 116. The longitudinal axis 116 may extend along the full length of the shaft 104 from the handle 102 to the guard 112. In other embodiments, the shaft 104 may have one or more curved portions. For example, the shaft 104 may include a deflection portion that deflects the outer sleeve 106 and the inner sleeve 108 from the longitudinal axis 116 and may define a second, distal axis 118. In some embodiments, at least a portion of the outer sleeve 106 and the inner sleeve 108 may be coaxial with the longitudinal axis 116. In other embodiments, at least a portion of the outer sleeve 106 and the inner sleeve 108 may be coaxial with the distal axis 118. In yet other embodiments, at least a portion of the outer sleeve 106 and at least a portion of the inner sleeve 108 may be coaxial with the longitudinal axis 116 and at least a portion of the outer sleeve 106 and at least a portion of the inner sleeve 108 may be coaxial with the distal axis 118.

The distal axis 118 and the longitudinal axis 116 may form a deflection angle 120 of the distal portion of the cannula device 100. The deflection angle 120 may be in a range having upper and lower values including any of 30°, 40°, 50°, 60°, 70°, 80°, 90°, or any values therebetween. For example, the deflection angle 120 may be in range of 30° to 90°. In another example, the deflection angle 120 may be in a range of 50° to 80°. In yet another example, the deflection angle 120 may be in a range of 60° to 70°.

FIG. 2 is a top view of the cannula device 100 of FIG. 1. The shaft 104 may extend from the handle 102 to the guard 112. The shaft 104 may contain and/or direct the outer sleeve 106 operably connected to the control member 114. While the control member 114 may control the relative position of the outer member to the handle 102 and shaft 104, the guard 112 may at least partially determine the position of the cannula device 100 relative to the patient's eye. The guard 112 may contact the sclera and/or other portion of the eye to position the cannula device 100 in a known reference position. In some ocular surgeries, the ability of the medical professional to visualize the procedure may be limited. The guard 112 may provide a known reference position to reduce the risk of unintended and/or undesired movement of the cannula device 100. In some embodiments, the handle 102 may include one or more markings on the handle to convey the relative position of the outer sleeve 106 and the control member 114. For example, the handle 102 may have a plurality of graduations thereon to convey to a user the distance to which the outer sleeve 106 has been moved in the distal direction relative to a retracted position and/or the distance to which the outer sleeve 106 has been moved in the proximal direction relative to the inserted position.

The guard 112 may have a distal face 122 and a proximal face 124. In some embodiments, the distal face 122 may have a flat surface. In other embodiments, at least a portion of the distal face 122 may be curved. In yet other embodiments, at least a portion of the distal face 122 may be concave in at least one direction. In at least one embodiment, the distal face 122 may be concave with respect to two directions. A distal face 122 that is concave in two directions may replicate the curvature of the eye and provide additional stability. In some embodiments, the guard 112 may have a solid distal 122 and/or solid proximal face 124. In other embodiments, the guard 112 may have a wire frame distal face 122 and/or wireframe proximal face 124. In some embodiments, the guard 112 may be ovoid, square, rectangular, other regularly shaped, irregularly shaped, or combinations thereof when viewed from a longitudinal direction. The distal face 122 may have a transverse dimension (transverse to the longitudinal axis 116) in one or more directions in a range having upper and lower values including any of 2.0 mm, 3.0 mm, 4.0 mm, 5.0 mm, 6.0 mm, 7.0 mm, 8.0 mm, or any value therebetween. For example, the guard 112 may have a transverse dimension in a range of 2.0 mm to 8.0 mm. In another example, the guard 112 may have a transverse dimension in a range of 3.0 mm to 7.0 mm. In yet another example, the guard 112 may have a transverse dimension in a range of 4.0 mm to 6.0 mm. In another embodiment, the guard 112 may have a thickness between the distal face 122 and the proximal face 124 in a range having upper and lower values including any of 1.0 mm, 2.0 mm, 3.0 mm, 4.0 mm, 5.0 mm, or any value therebetween. For example, the guard 112 may have a thickness in a range of 1.0 mm to 5.0 mm. In another example, the guard 112 may have a thickness in a range of 2.0 mm to 4.0 mm. In yet another example, the guard 112 may have a thickness of 3.0 mm.

FIG. 3 is a front view of the cannula device 100, showing the inner sleeve and the penetrative tip 110 extending distally from the distal face 122 of the guard 112. When in a retracted position, as shown, the penetration tip 110 may be in a proximal direction, exposing the inner sleeve 108. In some embodiments, the inner sleeve 108 be colored or otherwise include a visual indicator thereon to assist in identifying the position of the inner sleeve 108 during a medical procedure. In other embodiments, the penetrative tip 110 may be colored or otherwise include a visual indicator thereon to assist in identifying the position of the penetrative tip 110 during a medical procedure. In yet other embodiments, the inner sleeve 108 and the penetrative tip 110 may have different colors and/or visual indicators thereon to assist in identifying the relative position of the inner sleeve 108 and penetrative tip 110 during a medical procedure.

The penetrative tip 110 may include a sharpened edge 126 at the distalmost end of the penetrative tip 110. In some embodiments, the sharpened edge 126 may include a beveled edge, a ground edge, a serrated edge, a tapered edge, a single point, a plurality of points, or combinations thereof to allow the penetrative tip 110 to more easily puncture and/or penetrate bodily material, such as the sclera. In at least one embodiment, the distalmost point of the penetrative tip 110 may be located on a side of the penetrative tip 110 away from the guard 112 (i.e., on the bottom or outside of the curved portion of the penetrative tip 110) to reduce the risk of tearing of the sclera upon insertion and/or removal of the penetrative tip 110.

In some embodiments, the penetrative tip 110 may have a diameter in a range having upper and lower values including any of 0.020 inches (in) (0.51 mm), 0.022 in (0.56 mm), 0.024 in (0.61 mm), 0.026 in (0.66 mm), 0.028 in (0.71 mm), or any values therebetween. For example, the penetrative tip 110 may have a diameter in a range of 0.020 in (0.51 mm) to 0.028 in (0.71 mm). In other examples, the penetrative tip 110 may have a diameter in a range of 0.022 in (0.56 mm) to 0.026 in (0.66 mm). In yet other examples, the penetrative tip 110 may have a gauge in a range of 22 gauge to 25 gauge (Needle wire gauge). In yet further example, the penetrative tip 110 may have a gauge in a range of 23 gauge to 24 gauge.

Figure 4:
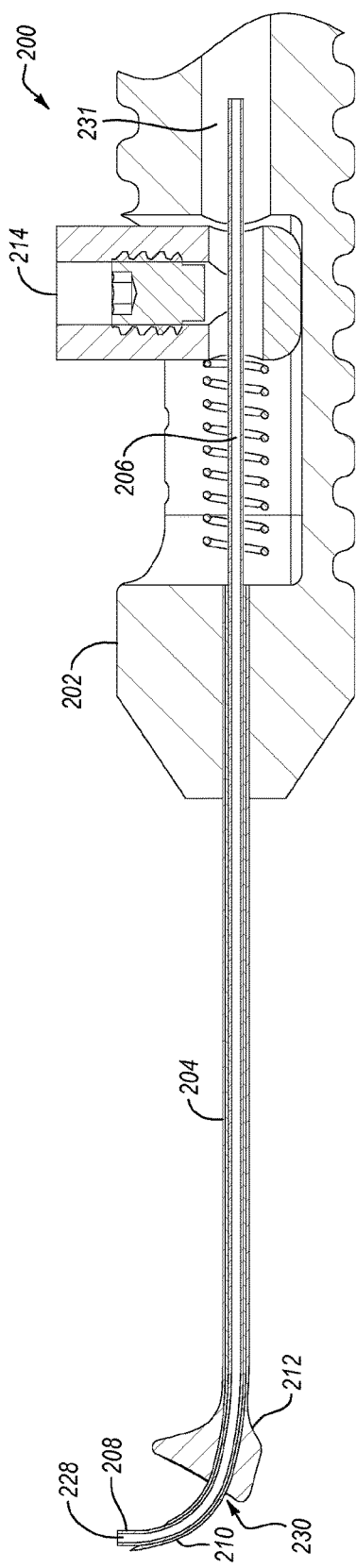
FIG. 4 is a side cross-sectional view of another embodiment of a cannula device having an internal fluid chamber, according to the present disclosure.

FIG. 4 is a side cross-sectional view of another embodiment of a cannula device 200 with an outer sleeve 206 and associated control member 214 in a retracted (i.e., proximal) position. The cannula device 200 may include a shaft 204 connecting a handle 202 to a guard 212. The shaft 204 may contain the outer sleeve 206, which may, in turn, contain an inner sleeve 208. The inner sleeve 208 may provide a fluid conduit 228 through at least a portion of the inner sleeve 208. In some embodiments, the fluid conduit 228 may extend from a distal end of the cannula device 200 through a deflection portion 230 and along the length of the shaft 204 to the handle 202. In the handle, an internal fluid chamber 231 may be in fluid communication with the inner sleeve 208. The internal fluid chamber 231 may receive fluid through the inner sleeve 208 from the body cavity, such as the SRF from the eye cavity and allow the user to remove the fluid from the patient.

FIG. 5 is a side cross-sectional view of another embodiment of a cannula device 300 with a penetrative tip 310 and control member 314 in a retracted (i.e., proximal) position relative to the handle 302. In some embodiments, a cannula device 300 may route fluid through a lateral fluid port 332.

The depicted embodiment of a cannula device 300 may have a fluid conduit 328 that does not extend through the entire length of an inner sleeve 308. In some embodiments, the fluid conduit 328 may terminate at a block 334 positioned in the inner sleeve 308. The block 334 may seal the fluid conduit 328, limiting or preventing the flow of a fluid proximal of the block 334. The fluid conduit 328 may extend proximally through the inner sleeve 308 to the fluid port 332. An external fluid chamber may be connected to the fluid port 332.

In some embodiments, the fluid port 332 may extend laterally through the inner sleeve 308, the outer sleeve 306 and the shaft 304. The inner sleeve 308 and the shaft 304 may be stationary relative to one another, and the outer sleeve 306 may be longitudinally slidable relative to the inner sleeve 308 and the shaft 304. When the outer sleeve 306 is in a retracted position, the fluid port 332 may provide fluid communication therethrough. When the outer sleeve 306 is in an inserted (i.e., distal) position, as shown in FIG. 6, an outer sleeve port 336 may be misaligned longitudinally with an inner sleeve port 338 and a shaft port 340. The fluid conduit 328 may have no exit to a fluid chamber while the outer sleeve 306 and control member 314 are in an inserted position.

When in an inserted position, the outer sleeve 306 may extend distally beyond the inner sleeve 308. For example, the sharpened edge 326 may be the distalmost point of the cannula device 300. The cannula device 300 may, therefore, be configured to penetrate the sclera of the eye while the fluid conduit 328 is sealed by the longitudinally misaligned outer sleeve port 336, inner sleeve port 338, and shaft port 340.

Figure 7:
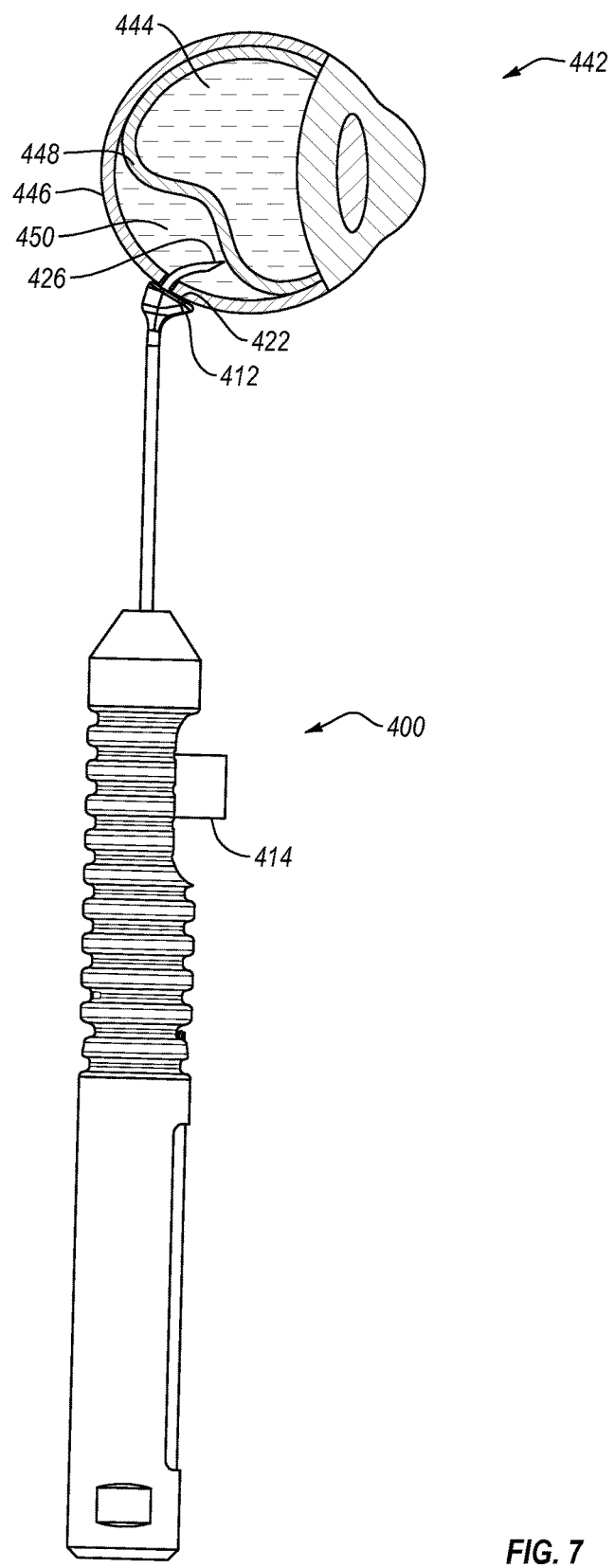
FIG. 7 is a schematic representation of an embodiment of a cannula device penetrating the sclera of an eye, according to the present disclosure.

Referring now to FIG. 7, an embodiment of a cannula device 400 in an inserted position is shown penetrating an eye 442. The eye 442 includes an eye cavity 444 filled with a vitreous fluid. RD is the detachment of the retina 448 from the sclera 446. In some cases, an opening through the retina 448 may allow the vitreous fluid to pass behind the retina 448 and allow the retina 448 to detach away from the sclera 446. Upon detachment of the retina 448 from the sclera 446, SRF 450 may begin to accumulate in the space between the detachment of the sclera 446 and retina 448. The SRF 450 may apply a fluid pressure that may limit or prevent the ability to reattach the retina 448 to the sclera 446. Removal of the SRF 450 may allow the reattachment of the sclera 446 and retina 448. Fluid communication through the cannula device 400 may also allow the introduction of therapeutic agents to the eye 442 via injections from the cannula device 400.

The control member 414 is shown in a distal position, which may be operably connected to the outer sleeve, and urging the sharpened edge 426 distally. In some embodiments, the sharpened edge 426 may penetrate the sclera 446, allowing at least a portion of the distal face 422 of the guard 412 to be in contact with at least a portion of the sclera 446. In other embodiments, the sharpened edge 426 may penetrate the sclera 446 and enter the space between the sclera 446 and the retina 448.

Figure 8:
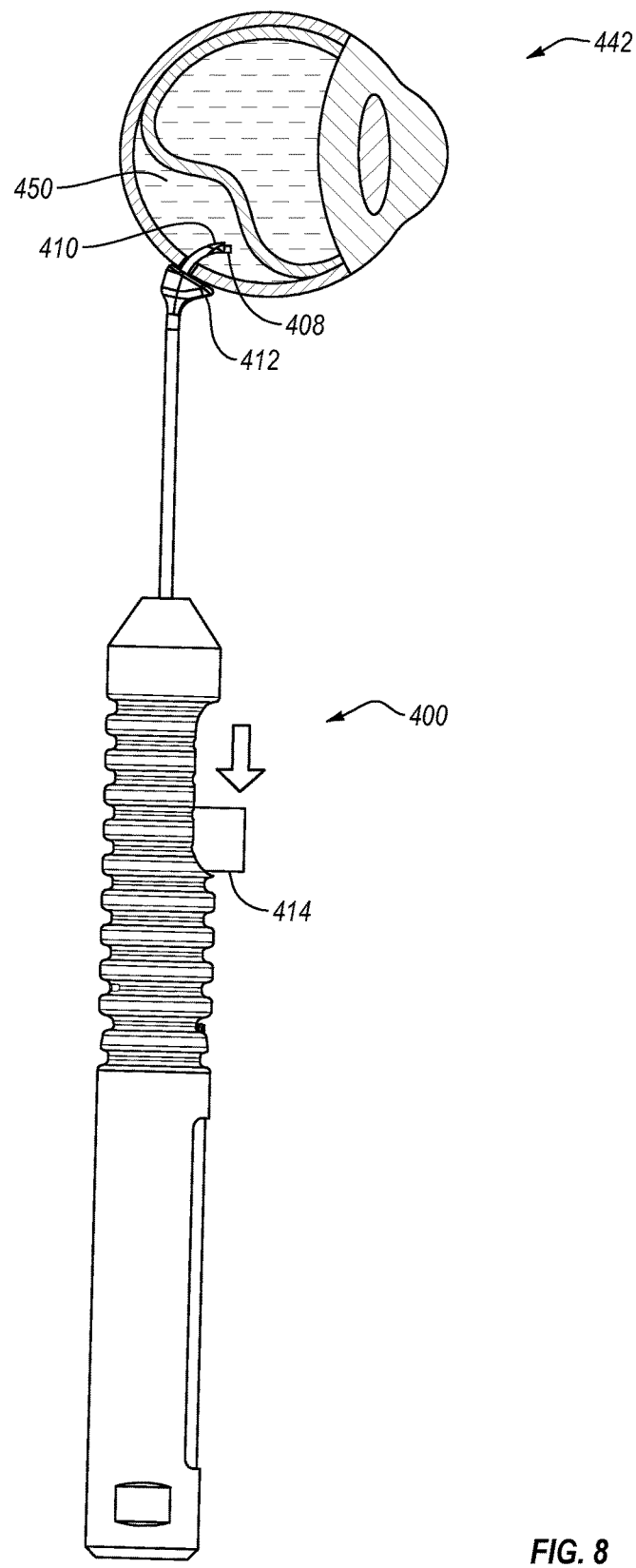
FIG. 8 illustrates the retraction of the outer sleeve of the cannula device in FIG. 7, according to the present disclosure.

FIG. 8 depicts the retraction of the penetrative tip 410 of the cannula device 400 upon proximal movement of the control member 414 to a retracted position. The penetrative tip 410 may move proximally and uncover the inner sleeve 408. The inner sleeve 408 may provide a fluid conduit to remove at least a portion of the SRF 450 from the space between the sclera 446 and the retina 448. The proximal movement of the penetrative tip 410 may allow and/or facilitate further insertion of the inner sleeve 408 (e.g., movement of the cannula device 400 toward the eye 442) because the inner sleeve 408 is blunt at the tip and therefore is less likely to damage the retina 448. As described herein, RD may occur when a retina 448 has an opening therethrough that allows accumulation of SRF behind the retina 448 from the eye cavity. Puncturing the retina 448 during removal of the SRF 450 may, therefore, result in further complications. After penetration of the sclera 446, the inner sleeve 408, and cannula device 400 as a whole, may be advanced distally while the penetration tip 410 is moved proximally. In some embodiments, the cannula device 400 may be advanced toward the eye 442 until the guard 412 contacts the eye 442.

Figure 9:
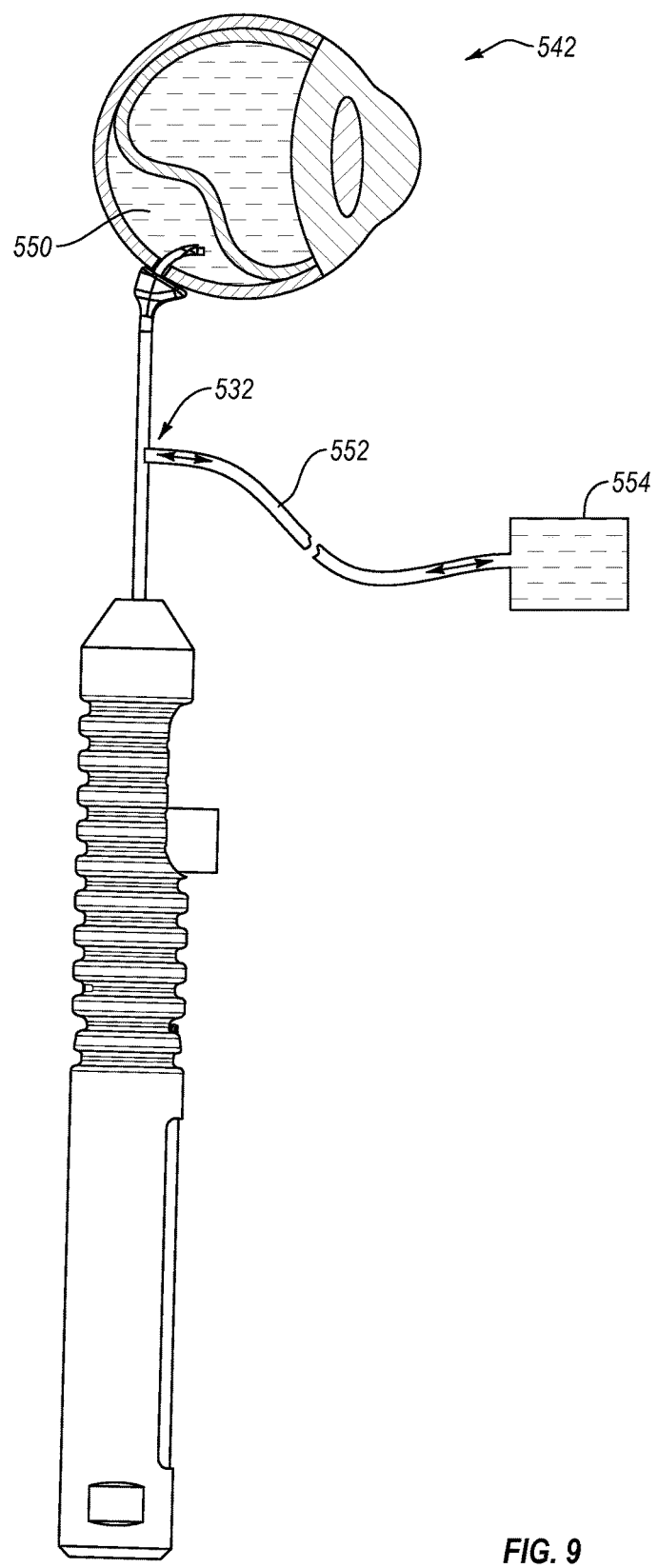
FIG. 9 illustrates removal of sub-retinal fluid ("SRF") from the eye through a lateral fluid port in an embodiment of a cannula device, according to the present disclosure.

FIG. 9 depicts an embodiment of a cannula device 500 having a lateral fluid port 532, similar to that described in relation to FIG. 5 and FIG. 6. Referring to FIG. 9, the lateral fluid port 532 may be in fluid communication with a drainage tube 552 that communicates with an external fluid chamber 554. The cannula device 500 may, thereby provide fluid communication between the eye 542 and the external fluid chamber 554 to drain SRF 550 from the eye 542 to the external fluid chamber 554. In some embodiments, the external fluid chamber 554 may apply a negative pressure (relative to the eye 542) to the SRF 550 to draw the SRF 550 from the eye 542 to the external fluid chamber 554. In other embodiments, the ocular pressure of the eye 542 may urge the SRF 550 from the eye 542. Conversely, as described herein, fluid from the external fluid chamber 554 can be injected through the cannula device 500 into the space under the retina (sub retinal space) in order to deliver medications or other therapeutic agents.

Figure 10:
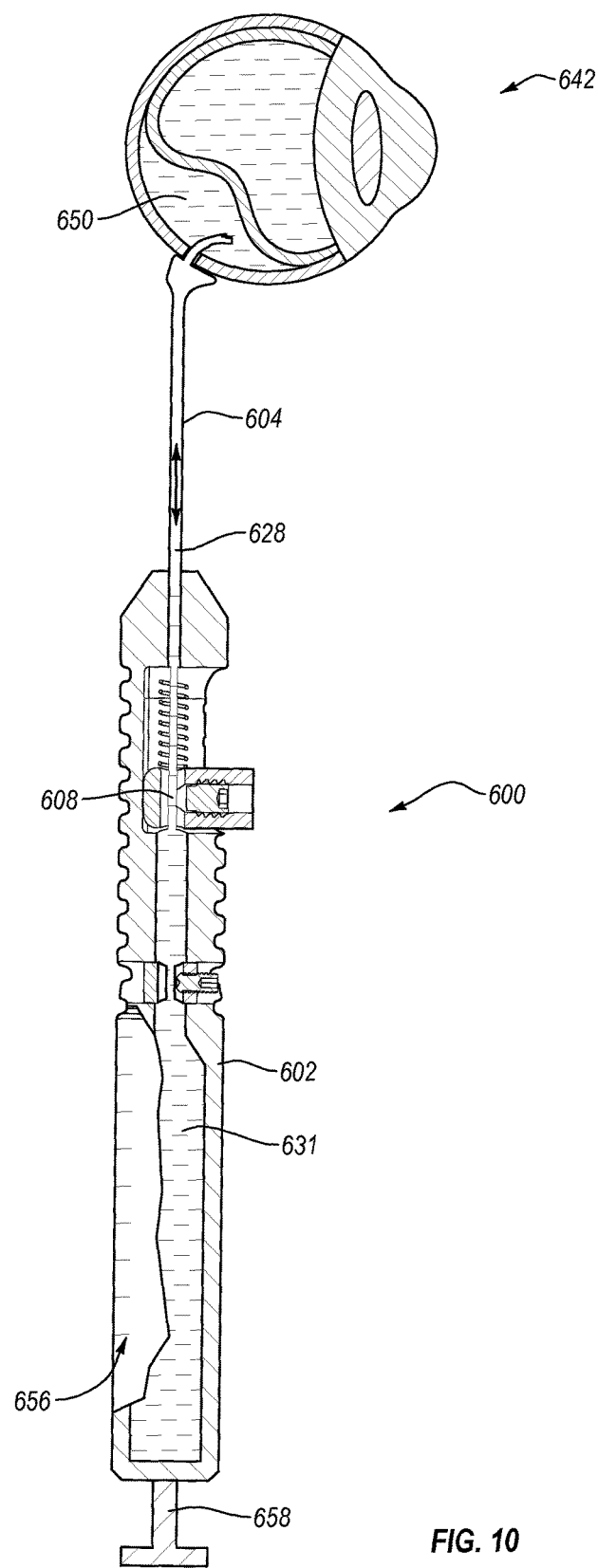
FIG. 10 illustrates removal of SRF from the eye into an internal fluid chamber of an embodiment of a cannula device, according to the present disclosure.

FIG. 10 illustrates an embodiment of removal of SRF 650 from an eye 642 into an internal fluid chamber 631 of a cannula device 600 and/or injection of a therapeutic agent from the internal fluid chamber 631 to the eye 642. The cannula device 600 may have a fluid conduit 628, as described in relation to FIG. 4, that extends from a distal end of the cannula device 600 through at least part of the shaft 604 and handle 602 to the internal fluid chamber 631. The internal fluid chamber 631 is shown in partially cutaway of the handle 602. The internal fluid chamber 631 may have a volume in a range having upper and lower values including any of 0.1 cubic centiliters (cc), 0.3 cc, 0.5 cc, 1.0 cc, 1.5 cc, 2.0 cc, 2.5 cc, 3.0 cc, or any values therebetween. For example, the internal fluid chamber 631 may have a volume in a range of 0.1 cc to 3.0 cc. In another example, the internal fluid chamber 631 may have a volume in a range of 0.5 cc to 2.0 cc. In yet another example, the internal fluid chamber 631 may have a volume of 1.0 cc.

In some embodiments, the internal fluid chamber 631 may include markings or graduations 656 to assist a user in identifying how much SRF 650 has been removed from the eye 642. For example, the graduations 656 may be inscribed, printed, written, embossed, or combinations thereof on the internal fluid chamber 631. In other examples, the graduations 656 may be inscribed, printed, written, embossed, or combinations thereof on the handle 602. In some embodiments, the internal fluid chamber 631 may be removable from the cannula device 600. For example, the internal fluid chamber 631 may be releasably connected to the handle 602 and/or the inner sleeve 608. The internal fluid chamber 631 and the inner sleeve 608 may be connected through a threaded connection, a press fit, a friction fit, a snap fit, a mechanical interlock, other selective connection mechanism, or combinations thereof.

In some embodiments, the internal fluid chamber 631 may include a plunger 658 or other device for applying a negative pressure to the internal fluid chamber 631 relative to the fluid conduit 628 and the ocular pressure of the eye 642. In other embodiments, a plunger 658 may allow for more precise control of the volume of SRF 650 removed from the eye 642. For example, the plunger 658 may allow a user to stop and/or control the rate of the drainage of SRF 650 from the eye 642.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

The terms "approximately," "about," and "substantially" as used herein represent an amount close to the stated amount that still performs a desired function or achieves a desired result. For example, the terms "approximately," "about," and "substantially" may refer to an amount that is within less than 5% of, within less than 1% of, within less than 0.1% of, and within less than 0.01% of a stated amount. Further, it should be understood that any directions or reference frames in the preceding description are merely relative directions or movements. For example, any references to "up" and "down" or "above" or "below" are merely descriptive of the relative position or movement of the related elements.

The present disclosure may be embodied in other specific forms without departing from its spirit or characteristics. The described embodiments are to be considered as illustrative and not restrictive. The scope of the disclosure is, therefore, indicated by the appended claims rather than by the foregoing description. Changes that come within the meaning and range of equivalency of the claims are to be embraced within their scope.

What is claimed is:

1. A cannula device, comprising
a shaft having a longitudinal axis;
an outer sleeve partially within the shaft and longitudinally slidable relative to the shaft, the outer sleeve having a penetrative tip at a distal end protruding from the shaft, the penetrative tip of the outer sleeve defining a distal axis at an angle to the longitudinal axis in a range of 30° to 90°;
an inner sleeve within the outer sleeve and stationary relative to the shaft, the inner sleeve having a fluid conduit extending through a longitudinal length thereof; and
a guard connected to the shaft and extending transversely to the longitudinal axis, the inner sleeve extending distally a chord length from the guard no more than 4.5 millimeters.

2. The cannula device of claim 1, wherein the guard has a deflection portion that deflects the outer sleeve such that the distal end of the outer sleeve is non-coaxial with the longitudinal axis.

3. The cannula device of claim 1, wherein the inner sleeve has a deflection portion that deflects the outer sleeve such that a distal portion of the outer sleeve is non-coaxial with the longitudinal axis.

4. The cannula device of claim 1, wherein the distal end of the outer sleeve is oriented between 30° and 90° from the longitudinal axis.

5. The cannula device of claim 1, wherein the guard has a concave distal surface.

6. The cannula device of claim 1, further comprising a control member being operably connected to the outer sleeve and configured to move at least a portion of the outer sleeve in a longitudinal direction such that the penetrative tip of the outer sleeve is configured to extend beyond the inner sleeve in a deployed configuration.

7. A cannula device, the device comprising:
a handle with a movable control member;
a shaft extending from the handle, the shaft having a proximal end, a distal end, and a longitudinal axis extending therebetween, the shaft having a deflection portion at the distal end that is not parallel to the longitudinal axis, the deflection portion defining a distal axis at an angle to the longitudinal axis in a range of 30° to 90°;
an outer sleeve partially within the shaft and longitudinally slidable relative to the shaft, the outer sleeve having a penetrative tip at a distal end and a position of the outer sleeve relative to the shaft at least partially determined by the control member;
an inner sleeve within the outer sleeve, the inner sleeve longitudinally stationary relative to the shaft; and
a guard connected to the distal end of the shaft, the guard extending radially away from the shaft and having a curved distal surface and a proximal surface, wherein the inner sleeve extends beyond a distal end of the guard.

8. The cannula device of claim 7, wherein the outer sleeve is made of a shape memory material.

9. The cannula device of claim 7, wherein at least a portion of the outer sleeve has a gauge in a range of 22 gauge to 25 gauge.

10. The cannula device of claim 7, further comprising a lateral fluid port extending transversely to the longitudinal axis through the shaft, the outer sleeve, and the inner sleeve.

11. The cannula device of claim 10, wherein the outer sleeve has a retracted position and an inserted position, wherein the lateral fluid port is formed by an outer fluid port and an inner fluid port, wherein the outer fluid port is longitudinally aligned with the inner fluid port in the retracted position and the outer fluid port is longitudinally misaligned with the inner fluid port in the inserted position.

12. The cannula device of claim 7, further comprising an internal fluid chamber in fluid communication with the inner sleeve.

13. The cannula device of claim 12, wherein the internal fluid chamber is releasably connected to the inner sleeve.

14. The cannula device of claim 7, wherein the inner sleeve extends distally a chord length from the guard no more than 4.5 millimeters.

15. A cannula device, the device comprising:
a shaft having a proximal portion having a longitudinal axis and a curved deflection portion distal of the proximal portion that deviates from the longitudinal axis of the proximal portion, the deflection portion defining a distal axis at an angle to the longitudinal axis in a range of 30° to 90°;
an outer sleeve within the shaft and longitudinally slidable relative to the shaft between a retracted position and an inserted position, the outer sleeve having a penetrative tip at a distal end and the outer sleeve being flexible to pass through the deflection portion of the shaft;
an inner sleeve within the outer sleeve, the inner sleeve longitudinally stationary relative to the shaft, the inner sleeve protruding distally from the outer sleeve when the outer sleeve is in the retracted position, the inner sleeve having a fluid conduit extending at least partially therethrough;
a guard connected to an exterior surface of the shaft at a distalmost end of the shaft, the guard extending radially away from the shaft and having a curved distal surface and a proximal surface; and
a fluid chamber in fluid communication with the fluid conduit of the inner sleeve.

16. The cannula device of claim 15, wherein the outer sleeve is a nickel titanium alloy.

17. The cannula device of claim 15, wherein the fluid chamber provides a negative pressure relative to the fluid conduit to draw fluid into the fluid chamber.

18. The cannula device of claim 15, wherein the deflection portion is longitudinally within the guard.

19. The cannula device of claim 15, wherein the shaft has a length between 2.0 cm and 3.0 cm.

20. The cannula device of claim 15, wherein the inner sleeve protrudes distally from the guard a chord length in a range of 2.0 mm to 4.5 mm.

* * * * *